United States Patent
Thengumpillil et al.

(10) Patent No.: US 6,500,974 B2
(45) Date of Patent: Dec. 31, 2002

(54) PROCESS FOR THE PREPARATION OF A MONOGLYCERIDE

(75) Inventors: Narayana Balagopala Kaimal Thengumpillil, Andhra Pradesh (IN); Vijayalakshmi Penumarthy, Andhra Pradesh (IN); Ananta Laxmi Ayyagari, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 82 days.

(21) Appl. No.: 09/796,083

(22) Filed: Feb. 28, 2001

(65) Prior Publication Data

US 2002/0120159 A1 Aug. 29, 2002

(51) Int. Cl.$^7$ ................................................ C11C 3/00
(52) U.S. Cl. ...................................................... 554/161
(58) Field of Search ......................................... 554/161

*Primary Examiner*—Deborah D. Carr
(74) *Attorney, Agent, or Firm*—Darby & Darby

(57) ABSTRACT

An improved process for the preparation of a monoglyceride by reacting a fatty acid and glycerol in the presence of a food grade polar solvent and avoiding the use of catalysts is provided.

8 Claims, No Drawings

PROCESS FOR THE PREPARATION OF A MONOGLYCERIDE

FIELD OF THE INVENTION

The present invention relates to a process for the preparation of a monoglyceride. The present invention particularly relates to a catalyst free improved process for the preparation of a monoglyceride by reaction of fatty acids with glycerol in the presence of solvent, under conditions that favour the predominant formation of monoglycerides.

BACKGROUND OF THE INVENTION

Monoglycerides constitute an important group of commercial derivatives which are used in food, cosmetic, pharmaceutical, lubricant and chemical industries. Monoglycerides find many applications as surfactants, mainly as emulsifiers, in a wide range of foods, cosmetics and pharmaceuticals. Monoglycerides are used in yeast-raised foods for retarding staling, cakes, icings and in the manufacture of margarine. Overall, this group of surfactants is the single most important one for food uses, representing about 75% of total emulsifier production. (*Bailey's Industrial Oil Fat Products*, Vol. 3, 5$^{th}$ Edition; *J. Am. Oil. Chem. Soc.*, 1976, 53, 400; *J. Am. Oil. Chem. Soc.*, 1984, 61, 255; *Angew. Chem. Int. Ed.*, 1988, 27, 42). Surfactants have a wide field of application in all those processes that involve working with interfaces. Nonionic surfactants especially esters of hydrophillic polyols, such as glycerine with fatty acids are of great interest (Falbe, J., *Surfactants in Consumer Products: Theory, Technology and Applications,* Springer-Verger New York, 1988). The most important commercial products are glycerol monostearate, monooleate, and monoricinoleate. Owing to their ability to form stable emulsions, monoglycerides such as monooleates are suitable as emulsifying components in aqueous fiber finishes, lubricant components, fine mechanical oils, water displacing oils and in grinding and polishing pastes (*J. Am. Oil. Chem. Soc.,* 1984, 61, 255). Monoglycerides are also reported to possess antibacterial properties. (Kabara, J. J., *The Pharmacological Effect of Lipids,* 2$^{nd}$ Edition, The American Oil Chemist's Society, Illinois, 1985). Recent developments include their use as drug delivery facilitators and bioadhesives (*Int. J. Pharma,* 1997, 147, 135; *Biomaterials,* 1997, 18, 63). They are reported to have a preventive effect on cardiovascular diseases. (*J. Am. Oil. Chem. Soc.,* 1993, 70, 745).

Many methods are described in prior art for the preparation of monoglycerides. Commercial manufacture of monoglycerides involves either glycerolysis of oils and fats at high temperature or direct esterification of fatty acids and glycerol with or without catalysts. Various types of homogenous and heterogenous catalysts are reported (*J. Am. Oil. Chem. Soc.,* 1976, 53, 400; *J. Am .Oil Chem. Soc.,* 1982, 59, 795A; *Nature,* 1960, 188, 56; *J. Am. Oil. Chem. Soc.,* 1962, 39, 345; *J. Am. Oil. Chem. Soc.,* 1964, 41, 727; *Chem Rev,* 1958, 58, 845; *J. Am .Oil. Chem. Soc.,* 1966, 43, 536; *J. Org. Chem.*1997, 62, 749; *J. Am. Oil. Chem. Soc.,* 1998, 75, 755). In all these processes the yields are typically in the range of 50%. Pure monoglycerides (over 90%) are obtained by molecular distillation which sometimes is a part of industrial process (*Fette. Seifen. Anstrichmittel,* 1983, 85, 443; *Chem Abstr* 1995, 123, 202772c).

Feuge and Gross (*J. Am. Oil. Chem. Soc.,* 1950, 27, 117) described preparation and purification of technical monoglycerides by modification of vegetable oils. They carried out reaction between fat and glycerol under hydrogen at atmospheric pressure using a glass vessel equipped with a stainless steel stirrer at 200–250° C. Monoglycerides to an extent of 40 and 60% were obtained by using approximately 20 and 45% glycerol respectively with sodium hydroxide as catalyst. Higher yields of monoglycerides are reported with soaps of iron, nickel, chromium or manganese as catalysts (U.S. Pat. No. 2,628,967). Choudhury reported glycerolysis of various oils for the preparation of monoglycerides and found that the maximum amount of monoglyceride formed by glycerolysis was about 45% (*J. Am. Oil. Chem. Soc.,* 1960, 37, 483).

A commercial non-solvent method of production involving glycerolysis of hydrogenated cottonseed oil with 40% glycerol (based upon the weight of fat used) at 250° C. yields about 60% of monoglycerides (*J. Am. Oil. Chem. Soc.,* 1979, 56, 752A). Castor oil glycerolysis was claimed to give 82% alpha-monoglycerides after 2 hours at 240° C. with 800 gm of oil and 2000 gm of glycerol, in the presence of carbon dioxide at 100 psi as a coblanketing catalytic agent. Under similar conditions coconut oil gave 74 and peanut oil 73% of monoglyceride. (Indian patent 71,979).

Recently glycerolysis of methyl stearate and tristearin has been carried out in the presence of alkyl guanidines, strong non-ionic bases as catalyst. The reaction was carried out at 10 mol % of 1,5,7-tri-azabicyclo(4.4.0)de-5-ene, 1,2,3-tricyclohexylguanidine or 1,3-decyclohexyl-2-n-octylguanidine resulting in monoglycerides in more than 90% selectivity at 50% conversion at 110° C. and 16 mbar pressure. They found that a higher conversion of about 80% resulted in lower selectivity (50–60%) for monoglycerides (*J. Am. Oil. Chem. Soc.,* 1998, 75, 755).

Choudhury also studied direct esterification of fatty acids with glycerol for preparation of monoglycerides in optimum yield and carried out reactions with excess glycerol at 180° C. in the presence or absence of alkaline catalysts and reported a maximum yield of 55–60% of monoglyceride (*J. Am. Oil. Chem. Soc.,* 1960, 37, 483). Selective esterification of glycerine to glycerol monooleate using a slightly basic ultrastable Y-Zeolite as catalyst was reported to give monoglycerides with a selectivity of about 90% (*Ind. Eng. Chem. Res.,* 1997, 36, 1524). Esterification of oleic acid with glycerol in the presence of superacidic sulfated iron oxide catalyst was reported (*J. Am. Oil. Chem. Soc.,* 1996, 73, 347). Monoglycerides were also obtained by esterification reaction over an acid catalyst. High pressure and temperatures were used to shift the equilibrium forward towards monoglyceride production. The product obtained was a complex mixture of 35–60% monoglyceride, 35–50% diglyceride, 1–20% triglyceride, 1–10% glycerine and fatty acids. The amount of monoglyceride was raised to 90–95% with 7–10% of 2-monoglyceride by molecular distillation. The advantage of pressure in carrying out glycerolysis is noteworthy. It appears to aid in the attainment of homogeneity and thus yields were improved.

Although the yields of monoglycerides by usual non-solvent methods of production are limited to about 60% of total glycerides, the use of solvents for the glycerolysis reaction enables a much higher conversion. Immiscibility of glycerol in fat like phases was overcome by carrying out the reaction in a solvent medium. Solvents like phenol, cresols, 1,4 dioxane, pyridine, chloroform and dimethyl formamide etc were used (*J. Am. Oil. Chem. Soc.,* 1982, 59, 795A; *Fat. Sci. Technol.,* 1995, 97, 347; *Chem Abst,* 1990, 112, 197639a,). Solvents offer the prospects of high yields at relatively low temperature but disadvantages in their handling, toxicity, noxious odors etc and the need to remove them completely from products explains the very limited efforts directed towards the synthesis in solvents. For example, Sunflower oil 10 parts, was reacted with glycerol, 20 parts at 120° C. with 0.3 parts of sodium bicarbonate in excess pyridine yielding 83% of total monoglycerides containing about 8% of 2-monoglyceride. In the absence of solvent, the reaction yielded 58% total monoglyceride containing 6% of beta-monoglyceride (*J. Am. Oil. Chem. Soc.,* 1979, 56, 751A). Kinetics of esterification reaction between glycerol and oleic acid in the presence of pyridine for production of partial glycerides was studied (*Fat. Sci. Technol,* 1995, 97, 347). The authors found pyridine to be a good solvent for the formation of partial glycerides.

The use of enzymes for the synthesis of MG was extensively studied (*Enzyme Microb. Technol.,* 1995, 17, 578; *J. Am. Chem. Soc.,* 1999, 76, 701). U.S. Pat. No. 5,153,126 describes a method for continous preparation of highly pure monoglycerides. The method comprises of esterification of fatty acid dissolved in a non-polar solvent at the interface between the nonpolar solvent phase and a polar solvent phase containing glycerol, water and dispersed lipase. The non-polar solvent phase is continuously taken out cooled, and the precipitated monoglycerides are isolated. The remaining solution is recycled back to the esterification system.

The enzymatic esterification of glycerol with dicarboxylic acids or esters was studied to produce mono-and/or diesterified glycerol adducts as synthons for biodegradable polymers and surfactants. They reacted glycerol or isopropylidene glycerol with sebacic or adipic acid esters. Reaction of dimethyl sebacate with isopropylidene glycerol gave the monoester in >95% yield, while reaction of glycerol supported on silica with dimethyl adipate gave only 40% yield of glycerol-mono-methyl adipate ester. Direct reaction of free glycerol with diester in the presence of water (<4%) gave a product containing 70% of glycerol-mono-methyl adipate ester (*J. Am. Oil. Chem. Soc.,* 1998, 75, 1545).

Lipase G catalyzed synthesis of monoglycerides in organic solvent hexane and water are reported (*J. Am. Oil. Chem. Soc.,* 1992, 69, 257). U.S. Pat. No. 5,270,188 claims preparation of glycerides having a high content of monoglycerides with Lipase G. U.S. Pat. No. 5,508,182 describes esterification of hydrophilic polyol by adsorption onto a solid support and employing a substrate immiscible solvent like hexane or t-butylmethyl ether. In this process the hydrophilic substrates were adsorbed on solid supports such as silica gel, diatomaceous earths or activated charcoals in order to promote the dispersions of the hydrophilic substrates within hydrophobic substrates and solvents. Enzymes used include lipases from *Mucor miehei,* and *Pseudomonas fluorescens,* glycosidases such as beta-galactosidase, proteases such as chymotrypsin and acid or alkaline phosphatases.

A process for the production of high purity beta-monoglycerides by lipase catalyzed transesterification (1,3-regiospecific lipase) is described in U.S. Pat. No. 5,316,927. Yield of monoglycerides is enhanced by means of enzymatic transesterification of triglycerides with aliphatic alcohols in a medium of supercritical carbon dioxide, with NOVOZYME 435™ enzyme. Aliphatic primary and secondary alcohols of 1–8 carbon atoms were used at lower reaction temperatures of 50–80° C., and a pressure of 3000 psi to 5000 psi diminishing the production of undesired side products thus increasing the reaction efficiency (U.S. Pat. No. 5,747,305).

U.S. Pat. No. 6,127,561 describes a process for the production of monoglycerides based on the glycerolysis of methyl esters. In this process the reaction is carried out with excess of glycerol at 130–160° C. and a vacuum of 200–400 mbar in the presence of alkaline catalysts. The reaction is stopped by fast cooling of the reaction mixture. The glycerol and methyl ester were separated by distillation at 230° C. and 4 mbar pressure in laboratory thin film evaporator. During the distillation the reaction proceeded further at resident time estimated at about 4–5 min. The residue contained 80% monoglyceride and 18% diglyceride.

The main difficulty in achieving high yields of monoglycerides either by glycerolysis or by direct esterification of fatty acids with glycerol is ascribed to the lack of sufficient degree of homogeneity of the reactants resulting in a product consisting of monoglycerides, diglycerides and triglycerides. Thus, many efforts were directed towards increasing the yields of monoglycerides. All the above procedures for the synthesis of monoglycerides are carried out in the presence of alkaline or acidic catalyst, which requires neutralization step. Glycerolysis reaction also generally requires two stringent conditions like very low levels of moisture and very low levels of FFA. And also the solvents reported may not be acceptable to production of food grade monoglycerides. Hence there is need for an alternative catalyst free process, but at the same time under homogenous environment, which gives high yields of monoglyceride.

To summarize, two methods are generally used for commercial production of monoglycerides. The first, non-solvent method requires high temperatures and generally results in a mixture of mono, di and triglycerides with low selectivity towards monoglycerides formation. Those prepared with heterogenous catalyst such as molecular sieves have questionable applicability if the product is intended for food use. The second method involving solvents which offers better selectivity have also major disadvantage in that the solvents employed are not food grade. Development of a simple process which may be carried out in the presence of solvent to provide the homogenous atmosphere would be advantageous.

OBJECTS OF THE INVENTION

The main object of the present invention is to provide a catalyst free process for the preparation of monoglycerides in presence of a solvent that is acceptable to the food industry and that also functions as a suitable solvent for glycerol.

Another object of the present invention is to use the monoglycerides thus obtained as emulsifiers in food, cosmetics and pharmaceutical preparations.

Yet another object of the invention is to use solvents which are completely safe, nontoxic and biodegradable.

Another object of the invention is to avoid the generation of aqueous effluents as in the case of homogeneous catalysts, thereby resulting in an environmentally friendly process.

Another object of the invention is to provide a process that has enhanced selectivity for monoglyceride over diglyceride.

STATEMENT OF THE PRESENT INVENTION

Accordingly the present invention provides a process for the preparation of a monoglyceride which comprises reacting a fatty acid and glycerol in a molar ratio in the range of 1:1 to 1:10, in the presence of a food grade polar solvent at a temperature in the range of 130–150° C. for a time period in the range of 3–6 hours to obtain said monoglyceride.

In one embodiment of the invention, the fatty acid used is a straight or branched chain fatty acid of acyl chain length C-8 to C-22.

In a further embodiment of the invention, the fatty acid used is selected from lauric acid and stearic acid.

In a further embodiment of the invention, the food grade polar solvent used is selected from methyl lactate and lactic acid.

In yet another embodiment of the invention, the molar ratio of said fatty acid to alcohol varies from 1:2 to 1:10.

In yet another embodiment of the invention, the unreacted glycerol and fatty acid are removed by dissolving the reaction mixture in diethyl ether and washing with water.

In still another embodiment of the invention, the conversion of said fatty acid is between 60–80%.

In yet another embodiment of the invention, the selectivity of monoglyceride over diglyceride is between 60–98%.

DETAILS OF THE PRESENT INVENTION

For achieving high yields of monoglycerides at low temperature, it is necessary to create a homogenous environment in the reaction medium. Hence the use of co-solvent was suggested by many workers in literature. The literature methods involves the use of pyridine, 1,4-dioxane, chloroform, phenols, cresols, and dimethyl formamide etc. as solvents in the presence of acidic or alkaline catalyst. These solvents are toxic and moreover the use of catalyst requires a neutralization step. Hence it would be more advantageous to carry out the reaction in a solvent which provides a homogenous atmosphere and at the same time is very safe to use the resultant monoglyceride in food grade preparations.

The present invention relates to a catalyst free process for synthesis of monoglycerides in presence of polar food grade solvents like methyl lactate and lactic acid, leading to high conversion and selectivities of monoglycerides over diglycerides. These solvents are completely safe, non-toxic and biodegradable.

A minor percentage of the formed monoglycerides are converted under the process conditions to lactylated monoglycerides (5–20%) which are also permitted food emulsifiers. The enhanced surface activity of the lactylated monoglycerides offers a product that is functionally superior to monoglyceride alone. As far as the authors are aware, lactic acid and alkyl lactates have not been used as a solvent for such reactions.

The following examples are given by the way of illustration and therefore should not be construed to limit the scope of the present invention.

EXAMPLE 1

Lauric acid and glycerol were reacted in a ratio of 1:2 in the presence of methyl lactate (10% of total wt of fatty acid and glycerol) at 130–140° C., for 5 hours. After the reaction the mixture was cooled, dissolved in diethyl ether and washed with water to remove unreacted glycerol and methyl lactate. The solvent was removed under reduced pressure, product was dried under vacuum and was analyzed by GC as trimethylsilyl derivative to determine the individual composition of fatty acid, monoglyceride, diglyceride, and triglyceride in the product. [Fatty acid (FA), 22%; Monoglyceride (MG), 52%; Diglyceride (DG), 22%; Triglyceride (TG), 1%; Lactylated monoglyceride (LMG), 3%].

The conversion of fatty acid was found to be 78% and selectivity of monoglyceride over diglyceride was 70%.

EXAMPLE 2

Lauric acid and glycerol were reacted in a ratio of 1:2 in presence of methyl lactate (50% of total wt of fatty acid and glycerol) at 130–140° C., for 5 hours. After the reaction the mixture was cooled, dissolved in diethyl ether and washed with water to remove unreacted glycerol and methyl lactate. The solvent was removed under reduced pressure, and product was dried under vacuum and was analyzed by GC as trimethylsilyl derivative to determine the individual composition of fatty acid, monoglyceride, diglyceride, and triglyceride in the product. (FA, 26%; MG, 59%; DG, 10%; TG, 1%; LMG, 4%)

The conversion of fatty acid was found to be 75% and selectivity of monoglyceride over diglyceride was found to be 85%.

EXAMPLE 3

Lauric acid and glycerol were reacted in a ratio of 1:4 in presence of methyl lactate (50% of total wt of fatty acid and glycerol) at 130–140° C., for 5 hours. After the reaction the mixture was cooled, dissolved in diethyl ether, and washed with water to remove unreacted glycerol and methyl lactate. The solvent was removed under reduced pressure, product was dried under vacuum and was analyzed by GC as trimethylsilyl derivative to determine the individual composition of fatty acid, monoglyceride, diglyceride, and triglyceride in the product. (FA, 24%; MG, 64%; DG, 7%; TG, 1%; LMG, 4%)

The conversion of fatty acid was found to be 76% and selectivity of monoglyceride over diglyceride was found to be 90%.

EXAMPLE 4

Lauric acid and glycerol were reacted in the ratio of 1:4 in presence of lactic acid (50% of total wt of fatty acid and glycerol) at 140–150° C., for 5 hours. After the reaction the mixture was cooled, dissolved in diethyl ether, and washed with water to remove unreacted glycerol and lactic acid. The solvent was removed under reduced pressure, the product dried under vacuum and was analyzed by GC as trimethylsilyl derivative to determine the individual composition of fatty acid, monoglyceride, diglyceride, and triglyceride in the product. (FA, 25%; MG, 56%; DG, 9%; TG, not present; LMG, 10%) The conversion of fatty acid was found to be 75% and selectivity of monoglyceride over diglyceride was found to be 86%.

EXAMPLE 5

Stearic acid and glycerol were reacted in a ratio of 1:3 in presence of methyl lactate (50% of total wt of fatty acid and glycerol) at 130–140° C., for 5 hours. After the reaction the mixture was cooled, dissolved in diethyl ether, and washed with water to remove unreacted glycerol and methyl lactate. The solvent was removed under reduced pressure, the product dried under vacuum and was analyzed by GC as trimethylsilyl derivative to determine the individual composition of fatty acid, monoglyceride, diglyceride, and triglyceride in the product. (FA, 38%; MG, 46%, DG, 6%; TG, 2%; LMG, 8%)

The conversion of fatty acid was found to be 62% and selectivity of monoglyceride over diglyceride was found to be 88%.

EXAMPLE 6

Stearic acid and glycerol were reacted in a ratio of 1:3 in presence of lactic acid (50% of total wt of fatty acid and glycerol) at 140–150° C., for 5 hours. After the reaction the mixture was cooled, dissolved in diethyl ether and washed with water to remove unreacted glycerol and lactic acid. The solvent was removed under reduced pressure, the product dried under vacuum and was analyzed by GC as trimethylsilyl derivative to determine the individual composition of fatty acid, monoglyceride, diglyceride, and triglyceride in the product. (FA, 37%; MG, 26%; DG, 14%; TG, 4%; LMG, 20%)

The conversion of fatty acid was found to be 63% and selectivity of monoglyceride over diglyceride was found to be 65%.

The main advantages of the present invention are:
1. The present invention is a catalyst free process for the preparation of monoglycerides by esterification between fatty acids and glycerol.
2. The reaction is carried out with the solvents which are completely safe, non-toxic and biodegradable.
3. As no catalyst is used, there is no generation of aqueous effluents as in the case of homogeneous catalysts. Hence the process is more environmentally friendly.
4. The reaction is carried out at relatively milder conditions than earlier reported methods.
5. The presence of minor concentrations of lactylated monoglycerides may provide a functionally superior product than monoglycerides alone.

We claim:

1. A process for the preparation of a monoglyceride which comprises reacting a fatty acid and glycerol in a molar ratio in the range of 1:1 to 1:10, in the presence of a food grade polar solvent at a temperature in the range of 130–150° C. for a time period in the range of 3–6 hours to obtain said monoglyceride.

2. A process as claimed in claim 1, wherein the fatty acid is a straight or branched chain fatty acid of an acyl length between C-8 to C-22.

3. A process as claimed in claim 2, wherein the fatty acid is selected from lauric acid and stearic acid.

4. A process as claimed in claim 1, wherein the food grade polar solvent is selected from methyl lactate and lactic acid.

5. A process as claimed in claim 1, wherein the fatty acid and glycerol is in a molar ratio in the range of 1:2 to 1:10.

6. A process as claimed in claim 1 wherein unreacted glycerol and fatty acid are removed by dissolving the reaction mixture in diethyl ether and washing with water.

7. A process as claimed in claim 1, wherein between 60–80% of the fatty acid is converted.

8. A process as claimed in claim 1, wherein the process yields a selectivity of monoglyceride over diglyceride between 60–98%.

* * * * *